Nov. 21, 1950 H. A. M. VERSCHUREN Plant Pat. 991
ROSE PLANT
Filed Jan. 12, 1950
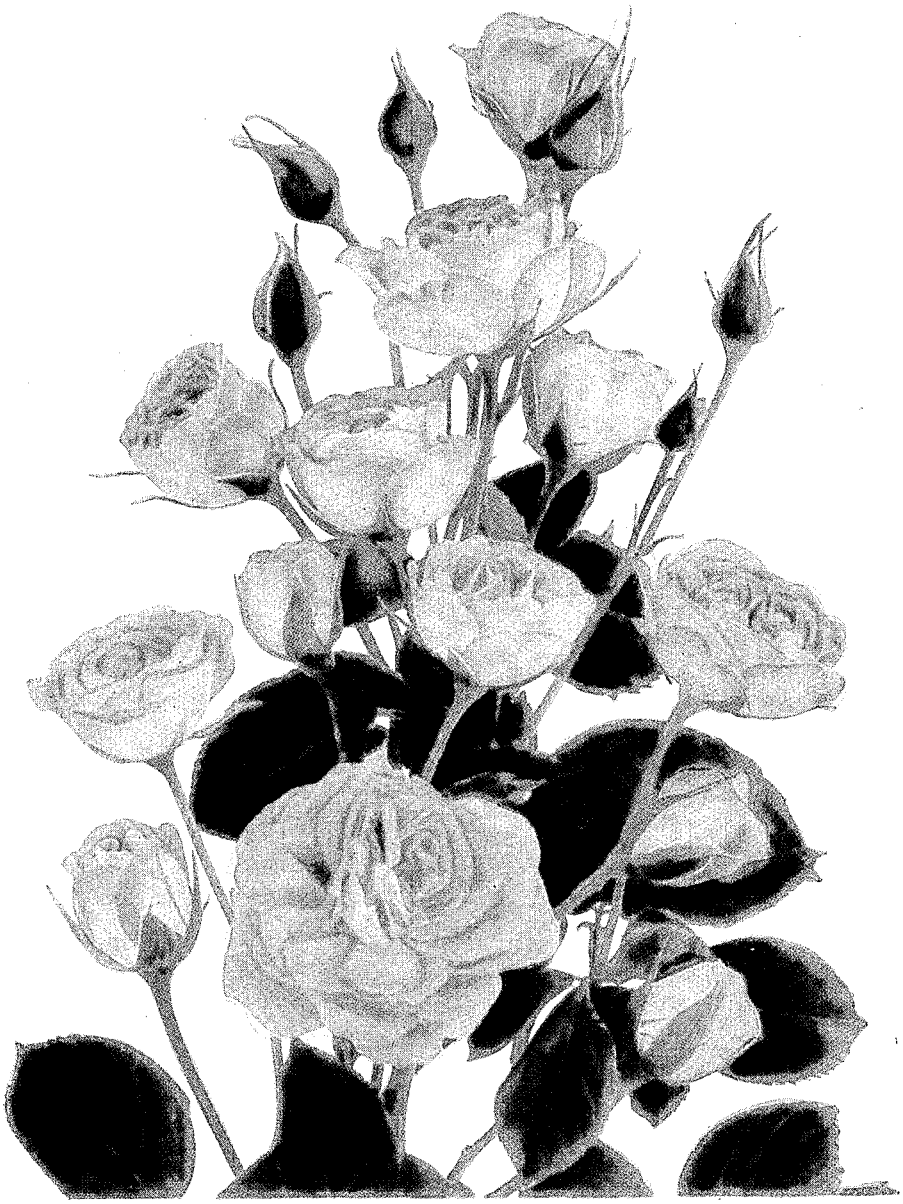
Inventor
H. A. M. Verschuren
By: Robb & Robb
Attorneys Patented Nov. 21, 1950

Plant Pat. 991

UNITED STATES PATENT OFFICE

991

ROSE PLANT

Hendrikus Antonie Maria Verschuren, Haps, Netherlands, assignor, by mesne assignments, to C. W. Stuart & Co., Newark, N. Y., a corporation of New York Application January 12, 1950, Serial No. 138,237

1 Claim. (Cl. 47—61)

The present invention relates to a new and distinct variety of hybrid polyantha rose plant of the floribunda type, resulting from the crossing of two varieties, not in distribution, but identified as hereinafter set forth.

This new variety has the outstanding characteristics distinguishing it from any other hybrid polyantha of the floribunda class now on the market, which I summarize as follows:

(1) Distinct two-tone color of flower similar to and as brilliant as the well-known hybrid tea variety "Condesa de Sastago" (unpatented).

(2) Contrast of color between the inside petals and the outside petals, such that when viewed from above, the flower is distinctly different in appearance than when viewed from the side. In connection with this feature it may be noted that although the contrasting colors are not the shades of "Forty-Niner" (Pl. Pat. No. 792), the degree of contrast is similar.

(3) Fragrance of the rose, which is more outstanding than that of any other hybrid polyantha of the floribunda type now in commerce. This fragrance is similar to that of the variety "Condesa de Sastago" but more intense, like the fruity fragrance of the old-fashioned red raspberry.

(4) Habit of change of color as the blooms develop from bud to full blown stages. In the bud stage, the color effect is yellow and carmine; as the flower opens the color becomes a definite carmine shade and seems to deepen in color for several days. After this stage, the color gradually changes to light rose. While the color is not the same as the "Peace" rose (Pl. Pat. #591), the day-to-day changes of the color are as definite.

Asexual reproduction of the new variety shows the foregoing characteristics come true to form and are established.

The accompanying drawing illustrates specimens of this new variety showing the flowers at their different stages of development from bud to fully open bloom.

This new variety was asexually reproduced at Newark, New York.

The following is a detailed description of the new variety, reference to color being in accordance with ordinary dictionary significance, except where indicated to be in accordance with Koster's Color Guide:

Type: Hardy; tall; bush; outdoor; seedling; for cut flowers and garden decoration.

Class: Hybrid polyantha of the floribunda type.

Breeding: Seedling.

*Seed parent.*—Unnamed seedling.

*Pollen parent.*—Unnamed seedling.

Propagation: Holds its distinguishing characteristics through succeeding propagations by grafting and budding.

*Flower*

Locality where grown: Newark, New York.

Flowers borne: Several to stem; pyramidal clusters on some; on strong, medium length stems.

Quantity of bloom: Free; outdoors and in greenhouse.

Continuity: Continuous.

Fragrance: Strong; fruity (similar to "Condesa de Sastago").

Bud:

*Peduncle.*—Medium long; medium heavy; erect and stiff; reddish-green; medium smooth; numerous green prickles.

*Before calyx breaks.*—Size—small. Form—long; pointed; ovoid; with a conspicuous neck; without foliaceous appendages on the surface of the bud; with slender bristle-like foliaceous parts extending beyond the tip of the bud equal to one-fourth of its length. Color—two-thirds Lemon Yellow, Plate #7, to one-third Crimson Carmine, Plate #41.

*As calyx breaks.*—Color—two-thirds Lemon Yellow, Plate #7, to one-third Crimson Carmine Plate #41.

*As first petal opens.*—Size—medium. Form ovoid. Color—outside—two-thirds Lemon Yellow, Plate #7, to one-third Crimson Carmine, Plate #41; inside—Oxblood Red, Plate #25. Opening—Opens up perfectly.

Bloom:

*Size, when fully open.*—Large; 2½ inches to 3 inches.

*Petalage.*—Very double; from 28 to 32 petals arranged irregularly.

*Form.*—Cupped and full; petals remaining at first rolled inward; becoming later, at maturity, tightly rolled outward.

Petals: Thick; with inside and outside shiny and velvety.

*Shape.*—Outside—obovate with apex flat with one notch. Intermediate—obovate with apex flat with one notch. Inside—obovate with apex flat with one notch.

This description of a newly opened flower was made from a rose grown in a greenhouse at Lyons, New York, in the month of January:

*Color.*—*Outside petal*—Outside surface—two-thirds Lemon Yellow, Plate #7, to one-third Crimson Carmine, Plate #41; inside surface—Crimson Carmine, Plate #41. *Intermediate petal*—outside surface—two-thirds Lemon Yellow, Plate #7, to one-third Crimson Carmine, Plate #41; inside surface—Crimson Carmine, Plate #41. *Inner petal*—outside surface—two-thirds Lemon Yellow, Plate #7, to one-third Crimson Carmine, Plate #41; inside surface—Crimson Carmine, Plate #41.

This description was made from a rose that was open for five days in a greenhouse at Lyons, New York, in the month of March:

*Color.—Outside petal*—outside surface—Solferino Red, Plate #40; inside surface—Carmine, Plate #29. Inside petal—outside surface—Solferino Red, Plate #40; inside surface—Carmine, Plate #29.

*General color effect.*—Newly opened flower—Solferino Red, Plate #40 and Carmine, Plate #29. Three days open—Solferino Red, Plate #40 and Carmine, Plate #29.

*Behavior.*—Drop off cleanly; after five days bud changes to Solferino Red, Plate #40.

*Flower longevity.*—On bush in garden—4 days in June. Cut roses grown outdoors, kept at living room tempratures—4 days in June. Cut roses grown in greenhouse kept at living room temperatures—6 days in March.

*Reproductive Organs*

Stamens: Medium number; arranged regularly about pistils.

Filaments: Medium length; yellow; most with anthers.

Anthers: Medium size; yellow-brown; open at various times.

Pollen: Moderate; gold.

Pistils: Many.

Styles: Even; long; thin; bunched.

Stigma: Yellow.

Ovaries: All enclosed in calyx.

Hips: Short; ovoid; with inconspicuous neck similar to Wichuraiana; green-gray; smooth; walls thick.

Sepals: Permanent; long; curled.
Color.—Light Yellow.

Seeds: Many; medium size.

*Plant*

Foliage:

*Leaves.*—5 leaflets; moderately abundant; medium large; soft; glossy.

*Leaflets.*—Oval; mucronate to base round.

*Color.* — *Mature* — upper surface — dark bronze; under surface—light green. *Young*—upper surface—green bronze; under surface—light green.

*Rachis.*—Heavy. Upper side—smooth. Under side—hairy.

*Stipules.*—Medium length; points turning out at an angle of less than 45°.

*Disease.*—Resistant to mildew and blackspot.

Growth:

*Habit.*—Bushy; upright; much branched.

*Growth.*—Free.

*Canes.*—Moderately heavy.

*Main stems.*—Green-bronze. *Thorns*—few; hooked downward; with long base. *Prickles*—few; green. *Hairs*—several; green.

*Branches.*—Green bronze. *Thorns*—few; hooked downward. *Prickles*—few; green-reddish. *Hairs*—several; green.

*New shoots.*—Green-brown. *Thorns*—few; long; hooked downward. *Prickles*—few; green-brown. *Hairs*—several; green.

I claim:

A new and distinct variety of hybrid polyantha rose plant of the floribunda type, characterized as to novelty by the contrasting colors of the flowers; by the change of the color of the blooms from the bud stage through the developments to the full blown stage, and by their intense and distinct fragrance, substantially as shown and described.

HENDRIKUS ANTONIE MARIA VERSCHUREN.

No references cited.